United States Patent [19]

Phillips et al.

[11] Patent Number: 5,537,854
[45] Date of Patent: Jul. 23, 1996

[54] ACOUSTIC NATURAL GAS FUEL SENSOR

[76] Inventors: Scott Phillips, 7002 E. 38th St., Tulsa, Okla. 74145; Richard M. Lueptow, 2509 Prospect Ave., Evanston, Ill. 60201

[21] Appl. No.: 66,703

[22] Filed: May 24, 1993

[51] Int. Cl.$^6$ .................................................. G01N 29/02
[52] U.S. Cl. .................. 73/24.01; 123/395; 123/DIG. 13
[58] Field of Search ..................... 73/24.01, 24.05, 73/24.06, 61.49, 597, 600; 123/350, 395, 402, 704, DIG. 13

[56] References Cited

U.S. PATENT DOCUMENTS

| 4,246,773 | 1/1981 | Haruta | 73/24.01 |
|---|---|---|---|
| 4,424,702 | 1/1984 | Schoenwolf | 73/24.01 |
| 4,596,133 | 6/1986 | Smalling et al. | 73/24.01 |
| 4,845,976 | 7/1989 | Johnson et al. | 73/23.2 |
| 5,036,669 | 8/1991 | Earleson et al. | 123/435 |
| 5,060,507 | 10/1991 | Urmson et al. | 73/24.01 |
| 5,131,224 | 7/1992 | Siewert et al. | 423/213.5 |
| 5,247,826 | 9/1993 | Frola et al. | 73/24.01 |
| 5,325,703 | 7/1994 | Magori | 73/24.01 |

FOREIGN PATENT DOCUMENTS

| 3009566 | 9/1981 | Germany | 73/24.01 |
|---|---|---|---|
| 4019808A | 1/1992 | Germany . | |

OTHER PUBLICATIONS

Hallewell et al., "A Sonar–Based Technique for the Ratiometric Determination of Binary Gas Mistures", *Nucl. Instr. & Meth. in Phys. Res.* A264:219–234 (1988).

Tinge et al., "Ultrasonic gas analyser for high resolution determination of binary–gas composition", *J. Phys. E. Sci. Instrum.* 19:953–956 (1986).

Hallewell, G. D., "A Sound Method for Measuring Gas Concentrations", *Research & Develop.* pp. 98–101 Sep. 1988.

*Primary Examiner*—Michael J. Brock
*Attorney, Agent, or Firm*—Hamilton, Brook, Smith & Reynolds

[57] ABSTRACT

A gaseous fuel analyzer having a flow through chamber equipped with sound producing means at one end and sound receiving means at the other for measuring an acoustic property of fuel flowing through the chamber and for numerically relating the acoustic property to the combustion character of the fuel.

26 Claims, 4 Drawing Sheets

ACOUSTIC NATURAL GAS FUEL SENSOR

BACKGROUND OF THE INVENTION

Natural gas has significant potential for providing an abundant, low cost alternate fuel for automotive use. One of the problems with natural gas as an alternate fuel for motor vehicles is that the composition of natural gas varies substantially from location to location and with the time of the year. Internal combustion engines tuned to operate efficiently on one composition of natural gas may operate poorly on another.

Natural gas supplies across North America range from 78% to 98% methane. This variation in composition results in problems in optimal performance of an automotive engine using natural gas as a fuel. Knock resistance of a gaseous fuel is measured in terms of the methane number, an analog to the octane number used to rate the anti-knock character of liquid fuels. For the range of natural gas available, the methane number ranges from 73 to 96. An engine that has been calibrated for optimal fuel economy and low tailpipe emissions for a particular composition or methane number of natural gas may function poorly on a different composition of natural gas.

Thus, knowing the methane number of a given fuel can assist in the periodic or continuous adjustment of motor vehicles using natural gas.

Since the molecular weight of methane is low, sound waves travel faster in pure methane than in methane combined with higher molecular weight gases such as nitrogen or ethane that often are present, in natural gas. Thus, the speed of sound in the gas can be used to determine the composition of the natural gas. The speed of sound in the gas also correlates to the methane number of the gas for the range of compositions typical of natural gas.

The present invention is based upon the above principles.

SUMMARY OF THE INVENTION

The invention resides in a gaseous fuel analyzer which employs a chamber through which a gaseous fuel flows. A sound producing means is located at the first end of the chamber and a sound receiving means is located at the opposite end of the chamber. A pulse generator sends a pulse to the sound producing means which propagates an acoustic wave through the chamber to the sound receiving means.

A timing circuit is employed to measure the elapsed time it takes the sound to pass through the gaseous fuel. The signal is received by an electronic circuit which produces a readout that may go to an engine or fuel controller or be used as a signal to create a human or machine readable number as, for example, at a dispensing station of such gaseous fuels.

Since the speed of sound is related to temperature as well as the gas through which it is transmitted, variations in temperature must be taken into account. Two schemes could be used to determine the temperature. First, an electrical temperature measurement device such as a thermocouple, thermistor, or resistance temperature detector (RTD) could be used to measure the temperature of the natural gas in the chamber. The output of the temperature measurement device would be used by the electronics to correct the measured sound propagation speed to account for temperature. A second alternative would be to use a second chamber, essentially identical to the first and equipped with sound producing and sound receiving means, that contains a known reference gas. A sound is sent through both gases and the output signals after passing through a filter and an amplifier are received by a race circuit which detects which sound wave reaches the detector first, that in the reference gas or in the test gas. The signals are processed in the race circuit and then a simple +/− output signal is sent, for example, to an engine controller.

The above and other features of the invention including various and novel details of construction and combination of parts will now be more particularly described with reference to the accompanying drawings and pointed out in the claims. It will be understood that the particular acoustic natural gas fuel sensor embodying the invention is shown by way of illustration only and not as a limitation of the invention. The principles and features of this invention may be employed in varied and numerous embodiments without departing from the scope of the invention.

DETAILED DESCRIPTION

A method of measurement of the speed of sound in natural gas is based on the following: The square of the speed of sound is a gas in given by $c^2=\gamma RT$. Here $\gamma$ is the ratio of specific heats which is a thermodynamic property of a gas and is defined as the specific heat at constant pressure divided by the specific heat at constant volume. R is the gas constant, and T is the temperature of the gas. The gas constant R is dependent upon the mass fraction of the components making up the natural gas. Methane has a gas constant of 0.520 kJ/kg-K, whereas typical natural gas contaminants such as ethane and nitrogen have smaller gas constants of 0.277 kJ/kg-K and 0.297 kJ/kg-K, respectively. The gas constant of a mixture of gases is equal to the sum of the gas constants of the components of the mixture each weighted by the mass fraction of the component. Although $\gamma$ varies slightly with composition, its variation is much smaller than the variation in R. Thus, the speed of sound is higher in pure methane than in methane mixed with ethane, nitrogen or other typical contaminants in natural gas.

The methane number can be related to the speed of sound empirically. As stated above, the methane number is a measure of the anti-knock properties of a gaseous fuel comparable to the octane number, used as a measure of the anti-knock properties of a liquid fuel.

The concept of using the speed of sound to determine a binary gas composition is not new. Several groups have evaluated the use of speed of sound techniques to determine binary gas composition and liquid composition and this is well documented. Many of these evaluations use time of flight measurements to find the speed of sound. Several permit flow of the fluid through a device. The prior art also covers the use of speed of sound to measure the composition in multi-component mixtures as well as binary mixtures.

Figure 1:
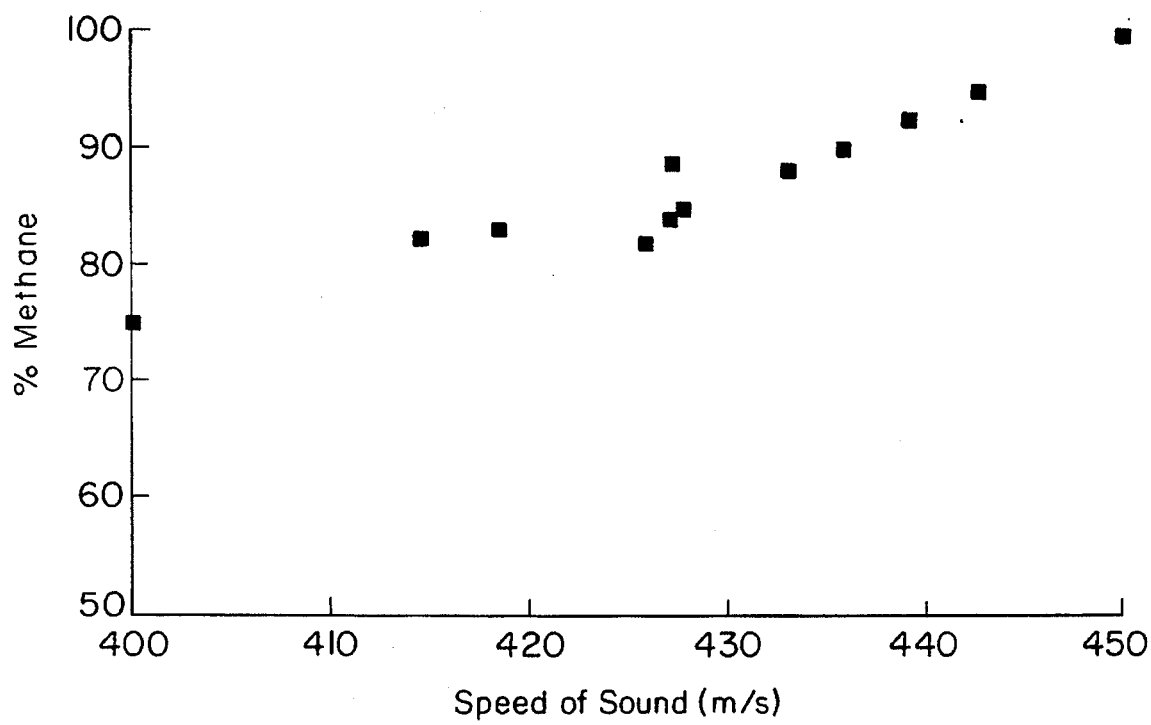
FIG. 1 is a graph of the fractions of methane in natural gas for typical gas compositions as a function of speed of sound in the gas.
Figure 2:
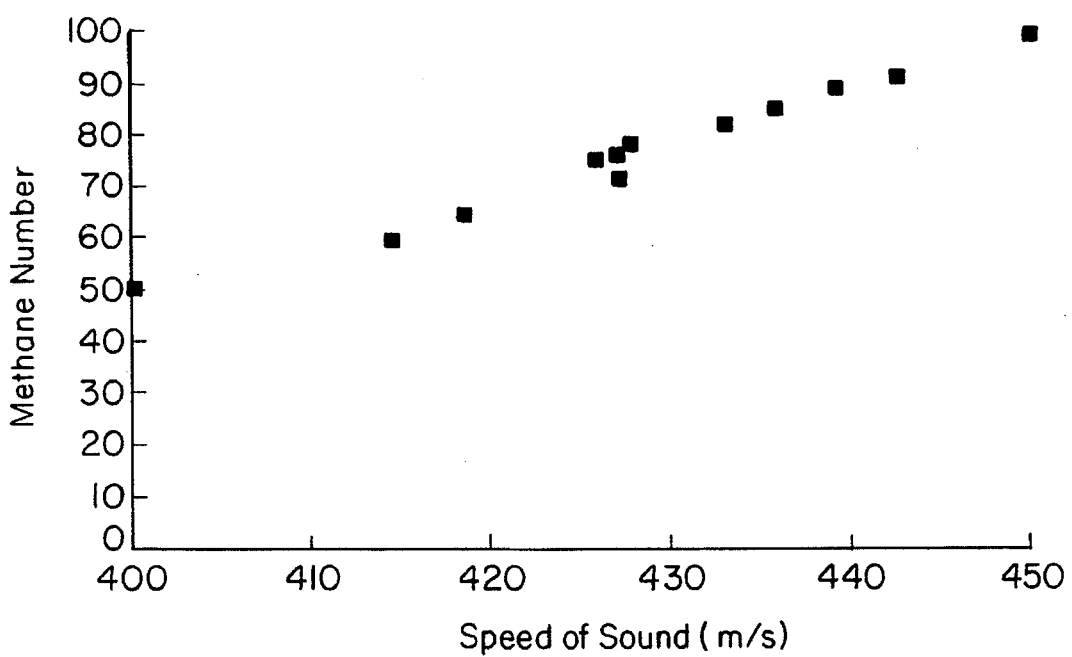
FIG. 2 is a graph of the methane number for typical natural gas compositions as a function of speed of sound in the gas.

The Gas Research Institute (GRI) has identified twelve typical gas compositions (Kubesh, "Effect of gas composition on octane number of natural gas fuels," GRI-92/0150, 1992) based on typical range of gas compositions throughout the United States (Liss, et al., "Variability of natural gas composition in select major metropolitan areas of the United States," GRI-92/0123, 1992). FIGS. 1 and 2 are based on these twelve typical compositions. The speed of sound for each gas composition was theoretically calculated. The percentage of methane in the gas or the methane number (Ryan and Callahan, "Effects of gas composition on engine performance and emissions," GRI-92/0054, 1991) was plotted as a function of the speed of sound.

FIG. 1 shows the percentage of methane in each of the eleven GRI typical gas compositions as a function of the theoretical speed of sound in the gas. There is a linear relation between the percentage of methane and the speed of sound. Not all samples fall exactly on a single line because the non-methane components can be various combinations of ethane, propane, butane, carbon dioxide or nitrogen. As a result, a narrow band of methane percentages may be related to a particular speed of sound. Nevertheless, the correlation between speed of sound and percentage of methane is very strong. The air-fuel ratio that a combustion engine should operate at for complete combustion ranges from 13.7 to 17.1 depending upon the gas composition. Although the percentage of methane in a gas does not completely determine the stoichiometric air-fuel ratio, it narrows the range of air-fuel ratios for full combustion.

FIG. 2 shows the methane number for each of the twelve GRI typical gas compositions as a function of the theoretical speed of sound in the gas. Again, there is a linear relation between the methane number and the speed of sound. Again as stated above, the methane number is a measure of knock resistance for a gaseous fuel, similar to the octane number for liquid fuel. Knock, pre-ignition detonation of the air-fuel mixture, can severely damage an engine, so it is crucial to be able to measure the knock. Increased compression ratios are often used to offset the inherent power losses in using a natural gas as a fuel. However, higher compression ratios are also more likely to cause knock if the methane number of the fuel is too low. Thus, it is necessary to know the methane number of the fuel. The speed of sound provides a good measure of the methane number for typical natural gas compositions as shown in FIG. 2.

Figure 3:
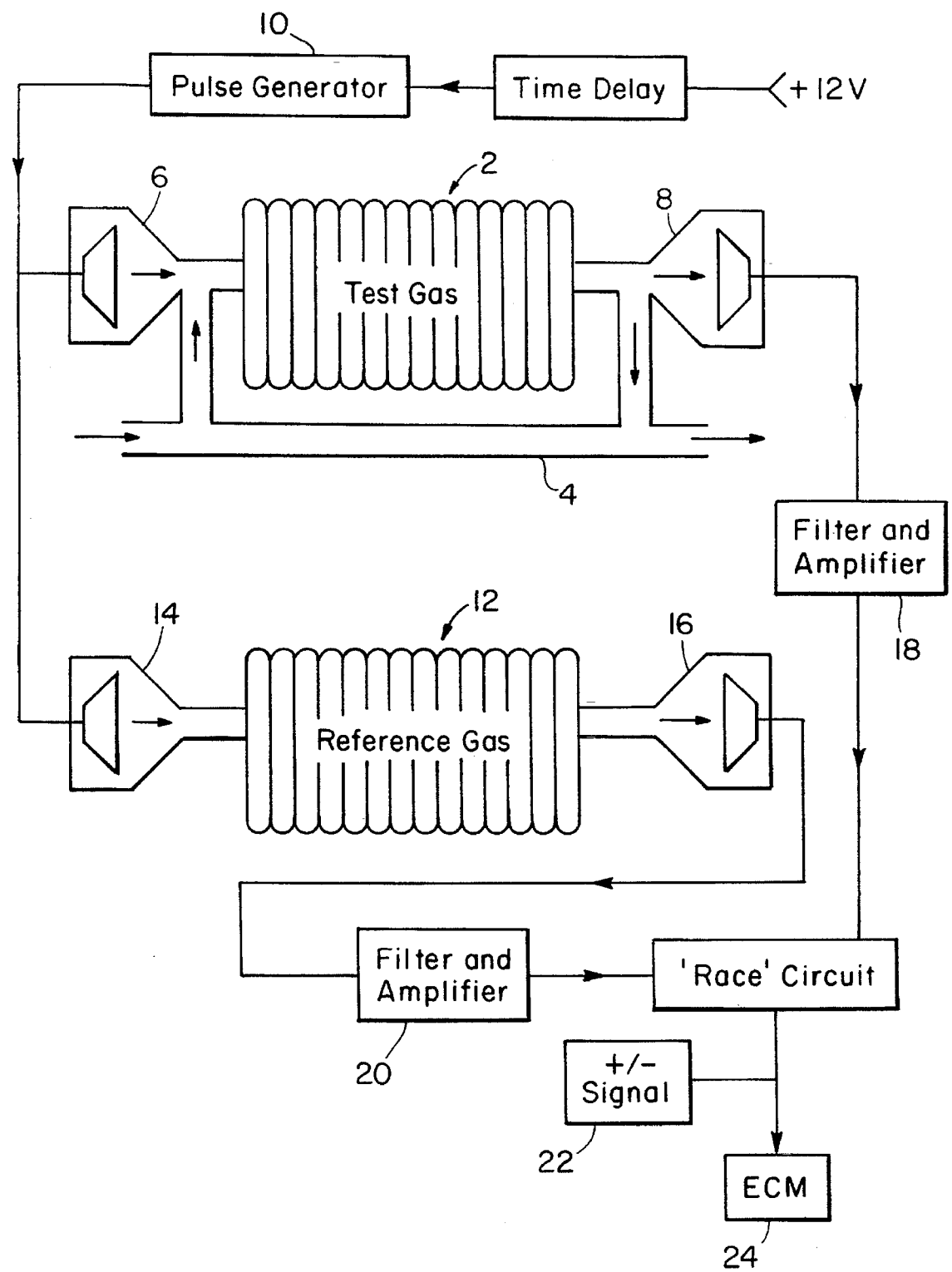
FIG. 3 is a schematic diagram of a fuel quality monitor embodying the invention incorporating a reference gas to account for temperature.

A schematic fuel quality monitor made in accordance with the present invention is shown in FIG. 3. It employs a flow-through chamber comprising a coiled 25 foot long tube 2 on the low pressure side of the pressure regulators (not shown) used to reduce the tank pressure of the gaseous fuel to the operating pressure. The coiled tube 2 is in parallel with the main fuel supply line 4 between the regulators and the engine. The tube 2 is of a size such that 2% to 10% of the natural gas flows through the coiled tube. At one end of the tube is a sound producing means such as a piezoelectric speaker or sender 6 and at the other end is a sound receiving means such as a piezoelectric microphone or receiver 8. An electrical pulse from a pulse generator 10 to the speaker 6 is used to generate a sound at one end of the tube. The sound wave propagates along the length of the tube to the microphone 8.

It will be appreciated that other acoustic properties instead of speed of sound may be employed in determining the methane number or "knock character". For example, the dispersion of sound or the resonance frequency of an oscillatory chamber could be substituted for the speed of sound.

Ideally, the length of time for the sound to travel the length of the coiled tube could be used to measure the speed of sound and, hence, the gas constant R, which is directly related to the gas composition. However, this is difficult for two reasons. First, the speed of sound is related to the temperature as well as the gas constant, R, so variations in temperature must be taken into account.

Second, the time for the sound wave to traverse the length of the coiled tube is very short, so it is difficult to measure without employing sophisticated electronics.

To solve both of these problems, there is a second coiled tube with a speaker 14 and a microphone 16 identical to the tube through which the natural gas flows. However, the second system contains only reference gas in the sealed tube. Both coiled tubes 2 and 12 are contained in a cylindrical case (not shown) that is 24 inches long and 6 inches in diameter. Because both the tube 2 measuring the sound in the test gas and the tube 12 with the reference gas are in close proximity, they should be at nearly the same temperature, solving the problem of temperature dependence in measuring the speed of sound. The use of a reference gas also solves the problem of the need for sophisticated electronics to measure the very short propagation time of the sound pulse along the length of the tube. Instead of timing the propagation time for the sound, the sound races in the test gas against the reference gas and passes through a filter and amplifier 18 and 20, respectively, to a conventional "race circuit" 21 which detects whether the sound wave reaches microphone 8 for in the test gas before it reaches microphone 16 for the reference gas or vice versa. A simple +/– output 22 is sent to an engine control module (ECM) 24 indicating whether the natural gas is better than the standard or worse.

When the second speaker/microphone system is not employed, the "race circuit" would not be employed and the output signal for the test gas is sent directly to the engine control module.

Figure 4:
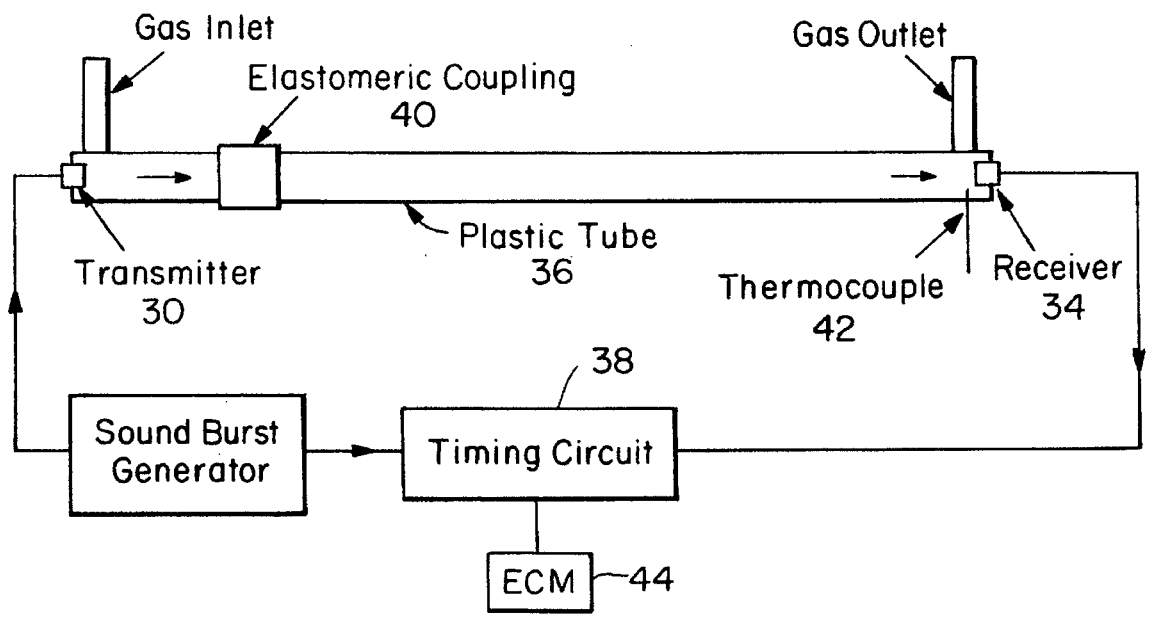
FIG. 4 is a schematic view of a second embodiment of the invention using a thermocouple to account for temperature.

As seen in FIG. 4, a preferred embodiment of the invention comprises a transmitter (speaker) 30 and receiver 34 (microphone) 34 at opposite ends of a chamber (tube) 36 through which the natural gas flows. A sound pulse emitted from the speaker 30 is received by the receiver 34. A timing circuit 38 is used to measure the time of flight of the sound pulse. The output of the timing circuit is sent to the engine control module (ECM) 40. Temperature compensation is achieved using either time of flight through a reference gas as described above or a temperature measurement instrument such as a thermistor or thermocouple 42. The speed of sound is related to the methane number through an appropriate empirical relation. The relationship between the methane number and speed of sound is shown in FIG. 2.

A sensor like that shown in FIG. 3 has been built using two 25 foot long flexible tubes 2 and 12 coiled within a pair of cans. Each tube has a piezoelectric buzzer and microphone, along with an output amplifier and band pass filter. A frequency of 4.2 kHz was found to produce a very clean signal in the system, so the band pass filter was set to pass frequencies between 4.0 and 5.3 kHz to minimize noise outside the frequency of interest. A simple race circuit comprises flip-flops to determine if the test gas or reference gas signal reached the end of the 25 foot tubes first when both piezoelectric buzzers were excited at the same instant.

Another embodiment is like that shown schematically in FIG. 4. An ultrasonic transmitter 30 and receiver 34 are at opposite ends of a 1 m (39 inch) long, 5 cm (2 inch) diameter rigid plastic tube 36. At a point along the length of the tube, an elastomeric coupling 44 is used to acoustically isolate the transmitter and receiver so sound is not propagated through the tube wall. Access for flow into and out of the tube is provided at each end of the tube. A thermocouple 42 is used to measure the temperature of the test gas. Currently, an oscilloscope and computer are used to monitor the signal to determine the speed of sound.

Figure 5:
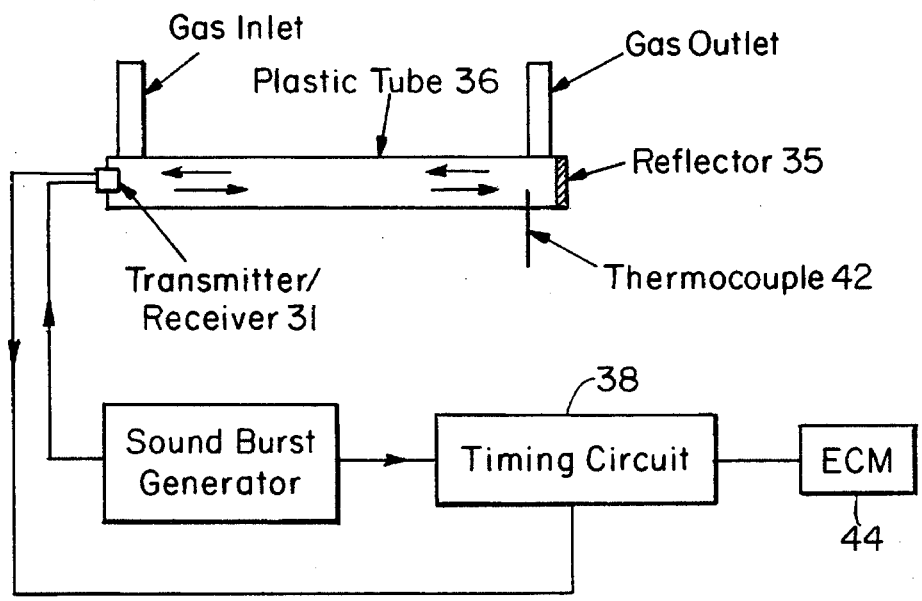
FIG. 5 is a schematic view of another embodiment of the invention.

Another embodiment replaces the receiver at the downstream end of the chamber with an acoustic reflector 35 and replaces the transmitter at the upstream end of the chamber with a combined transmitter/receiver 31, as shown schematically in FIG. 5. Piezoelectric devices are ideal transducers for application as a transducer/receiver, since such devices are mechanically identical whether they are working as a transmitter or receiver. Thus, a single piezoelectric device can provide both the transmitting and the receiving function. A sound pulse emitted at the transmitter/receiver propagates to the reflector and is reflected back to the transmitter/receiver. Thermocouple 42 is used to measure the temperature of the gas. This embodiment requires a shorter tube than that shown in FIG. 4 because the acoustic path length is two times the length of the tube. Another advantage of this embodiment is that the initial sound wave travels in the same direction as the gas flow and the reflected sound wave travels opposite to the gas flow. In this way, the additive effect of the combined gas velocity and sound velocity is canceled.

Figure 6:
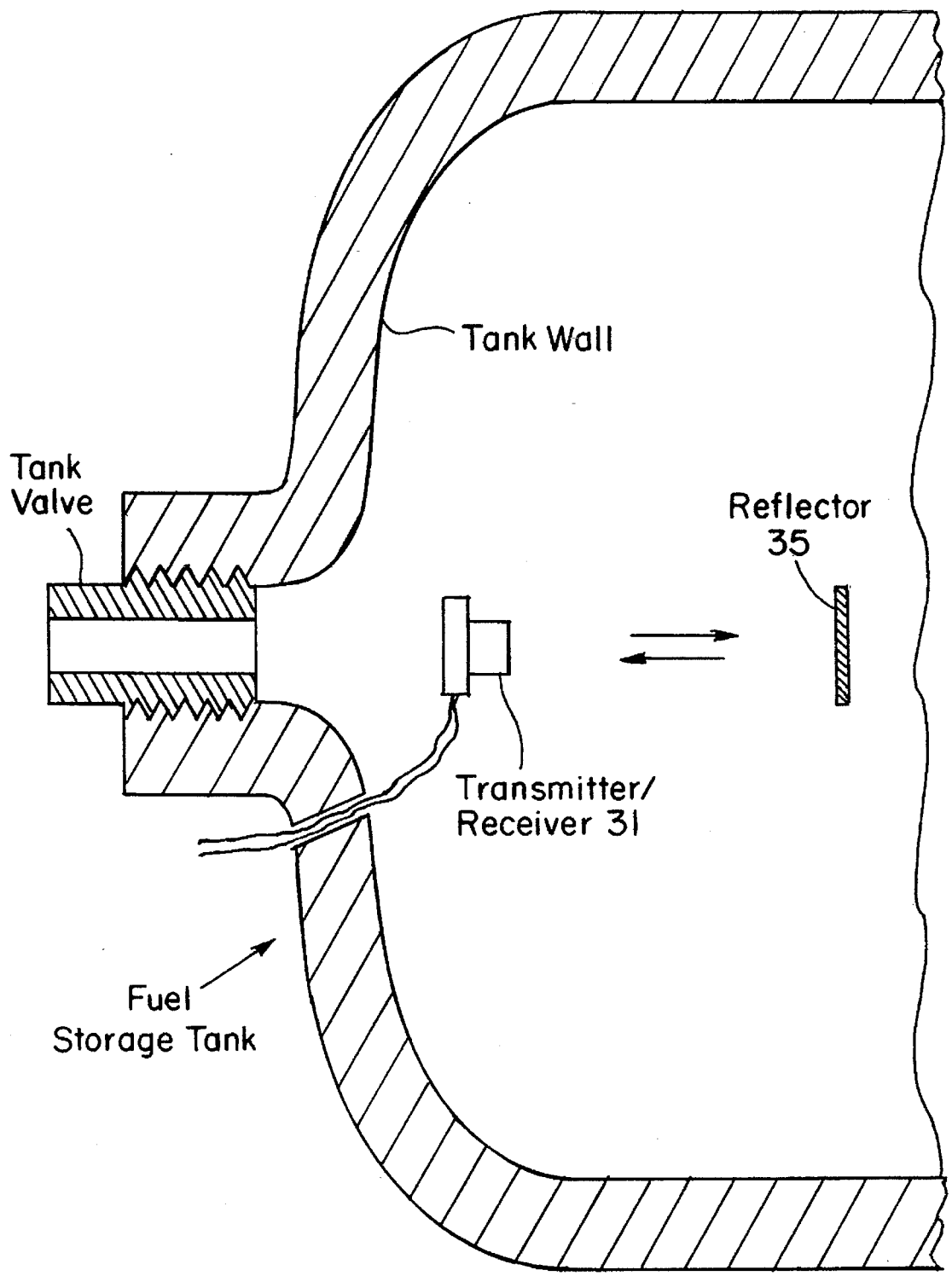
FIG. 6 is a partial sectional view of a fuel storage tank.

Still another embodiment uses the fuel storage tank as the chamber for the device, as shown schematically in FIG. 6. A sound pulse emitted at transmitter/receiver 31 propagates through the gas in the storage tank to reflector 35 and is reflected back to transmitter/receiver 31. Thermocouple 42 measures the temperature of the gas. The signals from transmitter/receiver 31 and thermocouple 42 are carried by electrical conduits to a sound burst generator, timing circuit, and ECM outside of the fuel storage tank (not shown).

This device has several advantages over other devices that could be developed for this application. First, it does not require combustion of the natural gas to determine composition, so it does not pollute or need to be vented to the atmosphere. Second, it is also substantially independent of the pressure of the compressed natural gas. Third, it requires no separation of the constituents of the natural gas before or during testing. Fourth, after its initial factory calibration, it requires no further calibration during use. Finally, the technology is simple and inexpensive enough for practical application to mass production natural gas vehicles.

What is claimed is:

1. A gaseous fuel analysis device comprising:

a chamber containing a gaseous fuel;

a sound producing means in the chamber;

a sound receiving means also in the chamber;

means for measuring an acoustic property of the gaseous fuel communicating with the receiving means;

means for numerically relating an acoustic property of the gaseous fuel to a combustion property of the gaseous fuel; and wherein the combustion property of the gaseous fuel is the anti-knock character.

2. Device according to claim 1 wherein the sound producing means and the sound receiving means are a piezoelectric transmitter and a piezoelectric receiver, respectively.

3. Device of claim 1 wherein there are means to produce an electrical signal corresponding to a combustion property of the gaseous fuel in communication with an engine controller such that information about the combustion property of the gaseous fuel is provided to the engine.

4. Device of claim 1 wherein the gaseous fuel is natural gas.

5. Device of claim 1 wherein the sound producing means is an electromechanical speaker and an electromechanical microphone.

6. Device of claim 1 wherein the sound producing means and sound receiving means are combined into one unit.

7. Device of claim 1 wherein the sound producing means and the sound receiving means are at opposite ends of the chamber.

8. A gaseous fuel analysis device comprising:

a chamber containing a gaseous fuel;

a sound producing means in the chamber;

a sound receiving means also in the chamber;

means for measuring an acoustic property of the gaseous fuel communicating with the receiving means;

means for numerically relating an acoustic property of the gaseous fuel to a combustion property of the gaseous fuel; and wherein the combustion property of the gaseous fuel is the methane number.

9. Device according to claim 8 wherein the sound producing means and the sound receiving means are a piezoelectric transmitter and a piezoelectric receiver, respectively.

10. Device of claim 8 wherein there are means to produce an electrical signal corresponding to a combustion property of the gaseous fuel in communication with an engine controller such that information about the combustion property of the gaseous fuel is provided to the engine.

11. Device of claim 8 wherein the gaseous fuel is natural gas.

12. Device of claim 8 wherein the sound producing means is an electromechanical speaker and an electromechanical microphone.

13. Device of claim 8 wherein the sound producing means and sound receiving means are combined into one unit.

14. Device of claim 8 wherein the sound producing means and the sound receiving means are at opposite ends of the chamber.

15. Device according to claim 8 wherein the sound producing means and the sound receiving means are a piezoelectric transmitter and a piezoelectric receiver, respectively.

16. A gaseous fuel analysis device comprising:

a first chamber containing a test gaseous fuel;

a sound producing means in the first chamber;

a sound receiving means also in the first chamber;

a second chamber containing a reference material;

a sound producing means in the second chamber;

a sound receiving means also in the second chamber;

means for producing and transmitting an electrical signal comparing the magnitude of an acoustic property of both the test gaseous fuel and the reference material in communication with the sound receiving means for both the first and second chambers; and wherein said first chamber is a fuel storage tank.

17. Device according to claim 16 wherein the sound producing means and the sound receiving means are a piezoelectric transmitter and a piezoelectric receiver, respectively.

18. Device according to claim 16 wherein the combustion property of the gaseous fuel is the methane number.

19. Device according to claim 16 wherein the combustion property of the gaseous fuel is the knock character.

20. Device according to claim 16 wherein the combustion property of the gaseous fuel is the fraction of methane.

21. Device according to claim 16 wherein the combustion property of the gaseous fuel is provided at a dispensing station for said gaseous fuel.

22. Device of claim 16 wherein there are means to produce an electrical signal corresponding to the combustion property of the gaseous fuel in communication with an engine controller such that information about the character of the gaseous fuel is provided to it.

23. Device of claim 16 wherein the gaseous fuel is natural gas.

24. Device according to claim 16 wherein the sound producing means is an electromechanical speaker and an electromechanical microphone.

25. Device of claim 24 wherein the speaker and microphone are combined into one unit.

26. Device of claim 16 wherein the sound producing means and the sound receiving means are at opposite ends of the first and second chambers.

\* \* \* \* \*